United States Patent
Schmiegel

(10) Patent No.: US 7,162,006 B2
(45) Date of Patent: Jan. 9, 2007

(54) METHOD FOR DE-SKEWING AN X-RAY PICTURE OF AN ITEM OF LUGGAGE

(75) Inventor: Armin Schmiegel, Hamburg (DE)

(73) Assignee: Yxlon International Security GmbH, Hamburg (DE)

( * ) Notice: Subject to any disclaimer, the term of this patent is extended or adjusted under 35 U.S.C. 154(b) by 115 days.

(21) Appl. No.: 10/985,623

(22) Filed: Nov. 10, 2004

(65) Prior Publication Data

US 2005/0169556 A1 Aug. 4, 2005

(30) Foreign Application Priority Data

Nov. 10, 2003 (DE) ................. 103 52 411

(51) Int. Cl.
G01N 23/04 (2006.01)
G06K 9/00 (2006.01)
G06K 9/32 (2006.01)

(52) U.S. Cl. ............. 378/57; 382/132; 382/289; 382/296

(58) Field of Classification Search .......... 378/57, 378/62, 98.8, 8; 382/100, 132, 275, 293, 382/289, 298; 345/660, 649, 667, 671
See application file for complete search history.

(56) References Cited

U.S. PATENT DOCUMENTS

| | | | | |
|---|---|---|---|---|
| 4,817,121 A | * | 3/1989 | Shimizu et al. | ............. 378/57 |
| 5,319,547 A | | 6/1994 | Krug et al. | |
| 5,638,420 A | | 6/1997 | Armistead | |
| 5,664,661 A | * | 9/1997 | Maier | ............. 198/412 |
| 5,671,297 A | | 9/1997 | Koppe et al. | |
| 5,870,449 A | | 2/1999 | Lee et al. | |
| 5,974,111 A | | 10/1999 | Krug et al. | |
| 6,252,929 B1 | | 6/2001 | Swift et al. | |
| 6,618,494 B1 | * | 9/2003 | Nonay et al. | ............. 382/132 |
| 6,628,745 B1 | * | 9/2003 | Annis et al. | ............. 378/21 |
| 6,904,121 B1 | * | 6/2005 | Claus et al. | ............. 378/21 |

FOREIGN PATENT DOCUMENTS

| | | |
|---|---|---|
| DE | 31 42 759 A1 | 5/1983 |
| DE | 37 08 843 A1 | 3/1988 |
| DE | 43 14 106 A1 | 11/1994 |
| DE | 43 16 847 A1 | 11/1994 |
| DE | 197 16 519 A1 | 6/1999 |

* cited by examiner

Primary Examiner—Edward J. Glick
Assistant Examiner—Anastasia S. Midkiff
(74) Attorney, Agent, or Firm—Squire, Sanders & Dempsey

(57) ABSTRACT

A method for the rectification of an X-ray picture (2a, 2b) of an item of luggage (2) during luggage screening with the following steps:
  recording the X-ray picture (2a, 2b) of the item of luggage (2) by means of a X-ray radioscopy device (11, 11a);
  geometric rescaling (7) of the X-ray picture (2a, 2b) whilst taking into consideration only the geometric data of the mapping geometry of the X-ray radioscopy device (11, 11a) and also the image data of the recording of the X-ray picture (2a, 2b) of the item of luggage (2), the beam path (10) being tracked for each detector element onto a respective preset plane;
  transmission of the rescaled, de-skewed X-ray picture (8a, 8b) to a display or image-processing apparatus (9).

5 Claims, 2 Drawing Sheets

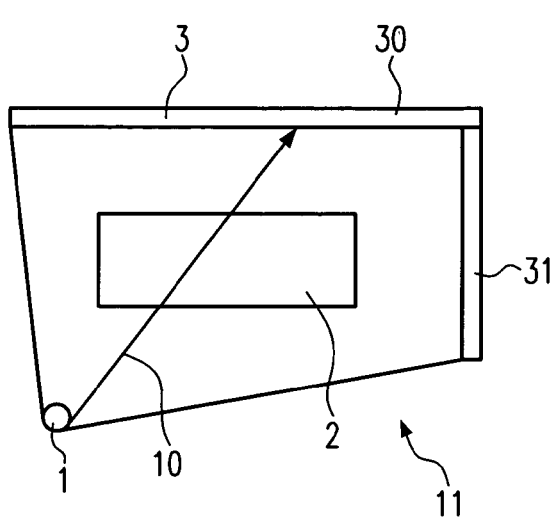
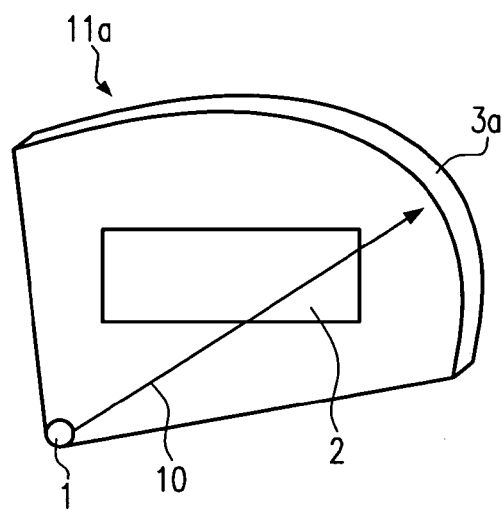
Fig.1a               Fig.1b
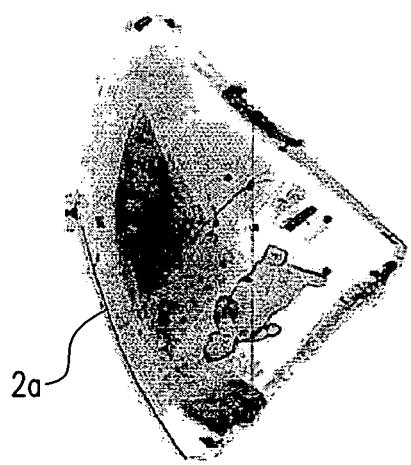
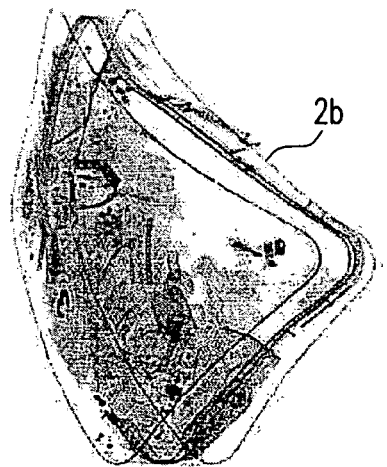
Fig.2a               Fig.2b

METHOD FOR DE-SKEWING AN X-RAY PICTURE OF AN ITEM OF LUGGAGE

CROSS REFERENCE TO RELATED APPLICATION

This application claims priority under 35 U.S.C. §119 to and incorporated by reference German Application No. 10352411.8-52/DE filed on Nov. 10, 2003.

FIELD OF THE INVENTION

The invention relates to a method for de-skewing an X-ray picture of an item of luggage during luggage screening.

BACKGROUND

Currently it is possible to analyze items of luggage completely for explosives. To do this, apparatuses are used which often work in the form of a line scanner. The X-ray beam transilluminates the item of luggage to be examined in slices. The fluoroscopic radiation is recorded with a line detector. L-shaped detectors are often used in the process. Due to their geometry there is a strong distortion of the recorded item of luggage, in particular in the region of the right angle. Such a skewed image is displayed on a monitor and examined by the security staff. As a result of the distortion it can happen that the items contained in the item of luggage cannot be correctly assessed. This leads to a security risk as dangerous items may not be recognized under certain circumstances.

SUMMARY

The object of the invention is therefore to provide a method, which makes possible a better recognizability of the items contained in an item of luggage.

In the method according to the invention, a clear rectification of the previously strongly skewed pictures of the item of luggage is achieved by means of geometric rescaling. For the geometric resealing according to the invention only the skewed picture of the item of luggage and the geometric data of the mapping geometry of the X-ray radioscopy device, by means of which the skewed picture was obtained, are required. The then de-skewed, i.e. geometrically rescaled, picture of the item of luggage is passed on to a display or image-processing apparatus so that the security staff can see an essentially rectified image of the items inside the item of luggage and thus can also classify these better.

An advantageous development of the invention provides that a line detector, in particular an L-shaped detector, is used as X-ray radioscopy device. Such an L-shaped detector has a very simple geometry with the result that the rectification can be determined very easily.

A further advantageous development of the invention provides that the X-ray picture is subjected to an optical calibration before geometric resealing. In particular the full dynamic range of the intensity values of the picture is used and a so-called histogram adaptation carried out.

A further advantageous development of the invention provides that the beam path is tracked for each detector element onto a respective preset plane, this preferably being carried out into a single plane. As a result a uniform reference surface is defined on which the geometric resealing is based.

A further advantageous development of the invention provides that the height of the item of luggage is determined, in particular by means of a light barrier. As a result it is possible that the optimum plane on which the geometric resealing is based can be established. In particular with tall items of luggage it is useful to have the preset plane on which the geometric resealing is based at half the height of the item of luggage parallel to the support surface.

Further advantageous developments of the invention are the subject of the dependent claims.

BRIEF DESCRIPTION OF THE DRAWINGS

Advantageous designs of the invention are explained in more detail using the drawings. There are shown in detail:

FIGS. 1a–b two schematically represented X-ray radioscopy devices with different geometries, FIGS. 2a–b representations of a respective X-ray picture of two different items of luggage with the X-ray radioscopy device of FIG. 1a, FIG. 3 a block diagram of a device on which the method according to the invention takes place, and FIGS. 4a–b representations of the two items of luggage FIGS. 2a–b after carrying out the method according to the invention.

DETAILED DESCRIPTION

Figure 3:
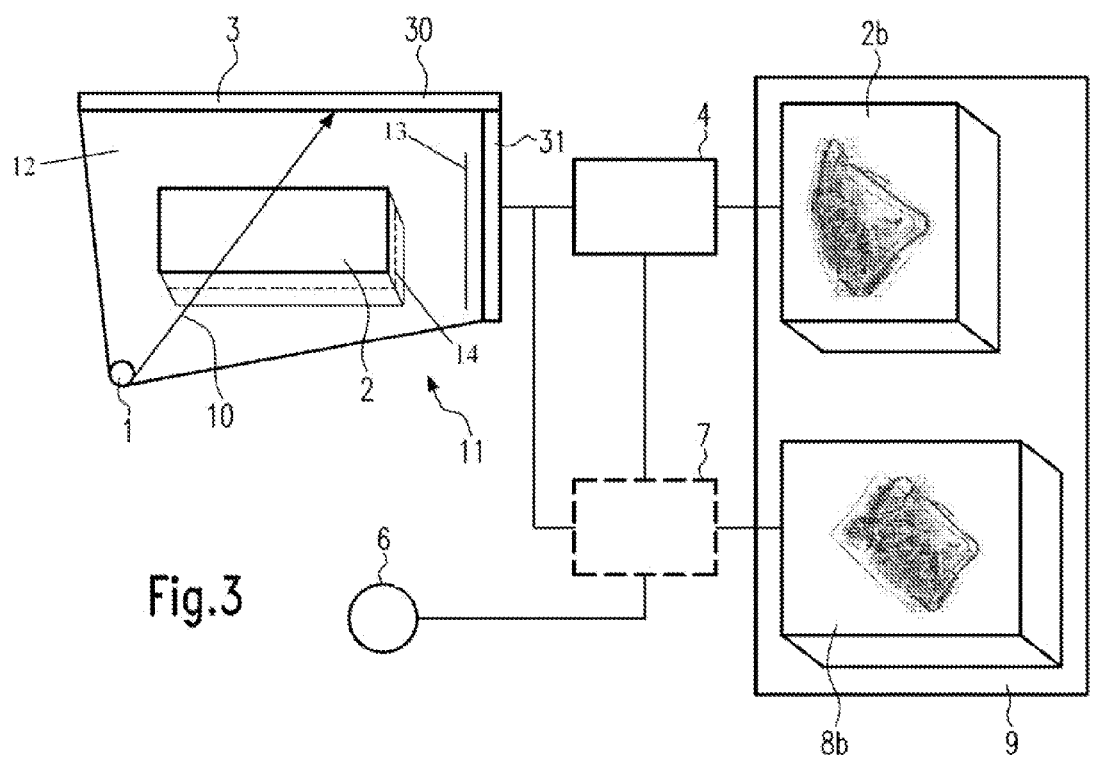

Two known X-ray radioscopy devices 11, 11a are shown schematically in FIGS. 1a and 1b. Each of these has an X-ray source 1 from which a beam path 10 sweeps an item of luggage 2. The transmitted X-radiation is recorded by a line detector 3, 3a. The geometric design of the line detectors 3, 3a is known in different forms. Only a common L-shaped detector unit is discussed below. Such a detector is called L-shaped detector 3.

FIGS. 2a and 2b show an X-ray picture 2a, 2b of different items of luggage 2 respectively which were recorded in a X-ray radioscopy apparatus 11 with L-shaped detector 3. A distortion along the horizontal axis is typical. The origin of this is in the angle resolution. A beam of rays with an angle width covers different-sized areas of the L-shaped detector 3. In particular at the point at which the horizontal detector 30 passes into the vertical detector 31, a strong distortion of the picture 2a, 2b of the item of luggage 2 is observed. This is the case in the left-hand region of the respective picture 2a, 2b in FIGS. 2a and 2b.

In addition, objects in the item of luggage 2 which are different heights are mapped under certain circumstances onto the same detector element. This distortion greatly hinders the analysis of the picture 2a, 2b of the item of luggage 2. The information density is not evenly distributed over the picture 2a, 2b. In some regions, in particular in the strongly compressed regions in the left-hand section of FIGS. 2a, 2b, a lot of data is stored in a very small area. Added to this is the optical distortion which occurs for the reasons described above which considerably hinder an interpretation of such pictures 2a, 2b. It can be emphasized that a comparison between X-ray pictures 2a, 2b of the same item of luggage 2 which were carried out by different line scanners is greatly impeded.

To date, attempts have not been made to solve this problem by carrying out a rectification of the pictures 2a, 2b of the item of luggage 2, but by means of dual-energy images. Such apparatuses serve to convey a suspicion, which is then examined by other analysis methods. To date another possibility was to change the position of the item of luggage 2 so that the strongly skewed region is moved into a less skewed region.

The schematic course of a method according to the invention for the rectification of a X-ray picture 2a, 2b of an item of luggage 2 is shown in FIG. 3. The method according to the invention is based on the method described above for the skewed recording of an X-ray picture 2a, 2b of an item of luggage 2 within an X-ray radioscopy device 11 with an X-ray source 1 and an L-shaped detector 3. The line-scan images obtained were regularly subjected to an optical calibration 4 or another known calibration or an image processing. With the dual-energy systems a color coding takes place in the process, which corresponds to the order number of the object inside the item of luggage 2. Suspicious regions were marked and the data of this preprocessing then transmitted to a display or image-processing apparatus 9. For example an image distribution computer was used which sends the image data to one or various operators.

The optical calibration 4 is still advantageously used. In addition however a transmission of the geometric data of the mapping geometry of the X-ray radioscopy device 11 is carried out. In addition the determination 6 of the position of the projection plane is carried out by measuring the height of the item of luggage 2 and these data likewise transmitted. The height of the item of luggage 2 can preferably be measured using a light barrier 13. The skewed X-ray picture 2b of the item of luggage 2 obtained due to the optical calibration 4 is subjected to the geometric rescaling 7. It is assumed that the X-ray picture 2b is the projection of an areal object. Whilst the actual intensity value of a detector element can be calculated from $$I = \int_0^1 ds f(s),$$

$$I = \int_0^1 ds \delta(s - s_0) f'(s).$$

The point $s_0$ lies on a particular plane. This plane can optionally be modified. For each detector element the beam path 10 is tracked onto the $s_0$ plane. The chosen $s_0$ plane is at half the height of the item of luggage 2 which has been previously established for example by means of a light barrier 13. It goes without saying that every other $s_0$ plane can also be used. The advantage of using the $s_0$ plane at half the height of the item of luggage 2 is that the maximum distortion is lowest as the distance of each object within the item of luggage 2 to the $s_0$ plane is at most half the height of the item of luggage.

The rectified X-ray picture 8b established by the geometric resealing 7 is passed to and displayed on the display or image-processing apparatus 9. It is thus possible for the security staff to obtain a predominantly rectified X-ray picture 8b of the item of luggage 2 and to be able to better recognize the objects contained therein.

Figure 4A:
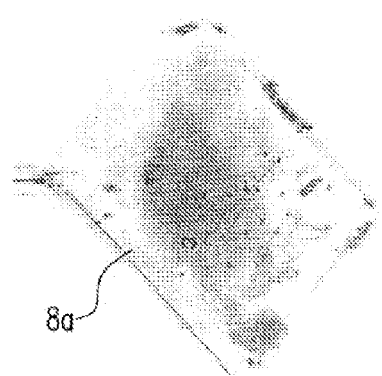
Figure 4B:
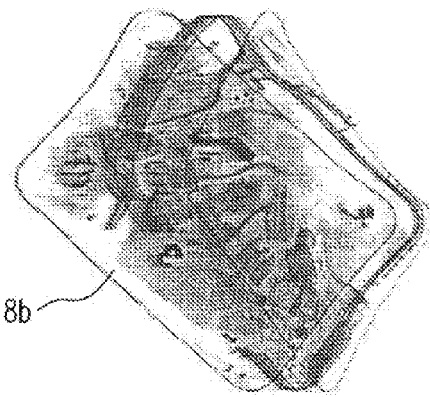

The rectified X-ray pictures 8a, 8b of the two items of luggage 2a, 2b shown in FIGS. 2a and 2b are shown in FIGS. 4a and 4b. In an embodiment of the invention, rectified X-ray pictures 8a, 8b may look clearer and the objects contained in the item of luggage 2 may be more easily recognized. The problem of distortion depending on the distance of an object inside the item of luggage 2a, 2b from the $s_0$ plane can be observed in FIG. 4b. The projection plane here was not set at half the height of the item of luggage 2, but at the height of the conveyor belt. Therefore objects, which are located near the conveyor belt are only slightly skewed. Objects, which are higher up, in particular near the top of the item of luggage 2, are more strongly skewed. However this can be corrected by changing the projection plane.

The regions in the left-hand halves of the images, which are strongly compressed in FIGS. 2a and 2b are greatly de-skewed in FIGS. 4a and 4b. As a result the analysis of objects, which are located in these regions is much simplified.

The method according to the invention can also be carried out in real time because of its low computational outlay. In fact, only the image data and the detector geometries are required. Thus every existing line-scan system can be equipped with such a method according to the invention without difficulty.

| LIST OF REFERENCE NUMBERS | |
|---|---|
| 1 | X-ray source |
| 2 | Item of luggage |
| 2a, 2b | X-ray picture of the item of luggage |
| 3, 3a | Line detector |
| 4 | Optical calibration |
| 6 | Determination of the position of the projection plane |
| 7 | Geometric rescaling |
| 8a, 8b | De-skewed X-ray picture of the item of luggage |
| 9 | Display or image-processing apparatus |
| 10 | Beam path |
| 11, 11a | X-ray radioscopy device |
| 12 | Support surface |
| 13 | Light Barrier |
| 14 | Preset Plane |
| 30 | Horizontal detector |
| 31 | Vertical detector |

What is claimed is:

1. Method for de-skewing an X-ray picture (2a, 2b) of an item of luggage (2) during luggage screening with the following steps:
   recording the X-ray picture (2a, 2b) of the item of luggage (2) by means of an X-ray radioscopy device (11, 11a);
   geometric rescaling (7) of the X-ray picture (2a, 2b) whilst taking into consideration only the geometric data of the mapping geometry of the X-ray radioscopy device (11, 11a) and also the picture data of the recording of the X-ray picture (2a, 2b) of the item of luggage (2), the beam path (10) being tracked for each detector element onto a respective preset plane (14);
   transmission of the rescaled, de-skewed X-ray picture (8a, 8b) to a display or image-processing apparatus (9);
   wherein the height of the item of luggage (2) is determined by a light barrier (13);
   wherein the preset plane (14) runs at half the height of the item of luggage (2) parallel to the support surface (12).

2. The method of claim 1, wherein the beam path (10) is tracked onto a single plane.

3. The method of claim 1, wherein the X-ray radioscopy device (11, 11a) has a line detector (3, 3a).

4. The method of claim 1, wherein the X-ray picture (2a, 2b) is subjected to an optical calibration (4) before the geometric rescaling (7).

5. The method of claim 3, wherein the line detector (3, 3a) includes an L-shaped detector.

* * * * *